United States Patent [19]

Bays et al.

[11] Patent Number: 4,650,488
[45] Date of Patent: Mar. 17, 1987

[54] BIODEGRADABLE PROSTHETIC DEVICE

[75] Inventors: F. Barry Bays, Seminole, Fla.; Richard L. Dunn, Birmingham, Ala.; Sam Marchand, Olive Branch, Miss.; Richard W. Treharne, III, Memphis, Tenn.

[73] Assignee: Richards Medical Company, Memphis, Tenn.

[21] Appl. No.: 610,965

[22] Filed: May 16, 1984

[51] Int. Cl.$^4$ .................. A61F 11/00; A61F 2/18; A61B 19/00
[52] U.S. Cl. .......................... 623/12; 623/11; 623/66; 128/1 R; 128/151; 604/264; 604/265
[58] Field of Search ............... 3/1, 1.4; 128/1 R, 151; 604/8-9, 45, 264, 265, 273, 287, 288; 623/1, 11, 66, 12

[56] References Cited

U.S. PATENT DOCUMENTS

| | | | |
|---|---|---|---|
| 3,530,860 | 1/1967 | Majoros | 623/12 |
| 3,620,218 | 11/1971 | Schmitt | 3/1.4 |
| 3,807,409 | 4/1974 | Paparella | 3/1 |
| 3,916,873 | 11/1975 | Wasserman | 623/12 |
| 4,168,697 | 9/1979 | Cantekin | 3/1 |
| 4,496,446 | 1/1985 | Ritter | 3/1 |

OTHER PUBLICATIONS

"Experimental Myringoplasty" by L. Feenstra et al., Inter. J. of Art. Org., vol. 3, #6, 1980, pp. 354-357.
"Controlled Release Technologies: Methods, Theory, and Applications" vol. II, Agis F. Kydonieus, CRC Press.
"Poly(Lactic Acid) and Poly(Lactic Acid-Co--Glycolic Acid) Contraceptive Delivery Systems" by Lee R. Beck and Thomas R. Tice in *Long-Acting Steroid Contraception*; Raven Press; NY, NY; 1983; Mishell ed.

*Primary Examiner*—Richard J. Apley
*Assistant Examiner*—Gregory Beaurage
*Attorney, Agent, or Firm*—Pravel, Gambrell, Hewitt & Kimball

[57] ABSTRACT

A prosthetic device formed of a biodegradable material and useful as a ventilation tube for insertion between the middle ear and the outer ear. The device includes a shaft with an axial passage, an inner flange and an outer flange. At least a portion of the outer surface of the shaft is tapered, with the taper increasing from the inner to the outer flange. The larger diameter outer flange and any attached portion of the shaft are, therefore, forced outwardly when the tapered portion of the shaft is in contact with animal tissue biodegrades before other portions of the prosthesis.

8 Claims, 4 Drawing Figures

BIODEGRADABLE PROSTHETIC DEVICE

BACKGROUND OF THE INVENTION

This invention relates primarily to prosthetic devices such as ventilation or drain tubes which are surgically inserted in the eardrum and are useful for equalizing pressure between the middle and outer ears and draining otitus media from the middle ear. More specifically, the invention relates to a ventilation tube which is at least partially biodegradable so that it can be removed without requiring the patient to undergo additional surgery after insertion.

While an exemplary embodiment of the subject invention is illustrated as a ventilation tube, the invention may also be applied to other prosthetic devices which communicate between various portions of the body or between the atmosphere and the body.

With particular reference to the ventilation tube application, the typical remedy for middle ear effusion is a myringotomy surgical procedure, which involves cutting a slit in the eardrum to relieve a buildup or reduction of pressure in the middle ear cavity. A variety of ear ventilation tubes for insertion into such a slit have been introduced over the years in an attempt to keep the eardrum slit open for a sufficient period of time following the surgery to allow pressure to equalize between the middle and the outer ears. Since a slit in the eardrum tends to heal within twenty-four hours, a plastic tube has been used to keep the slit open and allow the equalization of pressure.

Problems have developed when such ventilation tubes have fallen out of the eardrum too soon, which requires surgical insertion of another tube, or when the tube is taken out too late, which exposes the middle ear to possible infection from water or other substances migrating from the outer ear and possible perforation of the eardrum. Such ventilation tubes have also fallen into the middle ear or have had to be removed by additional surgery. Most of the currently used ventilation tubes, if not extruded naturally, are removed and are not intended to be left in the ear permanently.

SUMMARY OF THE INVENTION

According to the present invention, a prosthetic device such as a ventilation tube for the middle ear has been developed which solves the problems discussed above and eliminates the necessity for an additional surgical procedure in order to remove the device. This is accomplished by forming at least a portion of the tube of a material that dissolves on contact with water such as found in body fluids while the remainder retains at least some structural integrity. With this structure, when the section in contact with the water such as found in body fluids in, for example, an eardrum, dissolves, the remainder of the prosthesis loses structural integrity such that the portion outside the eardrum merely falls out while the portion inside the eardrum falls into the middle ear cavity and is dissolved therein. Thus, the tube is removed without surgery or outside intervention. While the invention is directed toward a ventilation tube for the middle ear, this type of structure can be used in other types of implantable prostheses which must be removed at some period of time after insertion.

For the ventilation tube embodiment, the section formed of a material dissolvable on contact with animal body fluids, e.g. biodegradable material, is formed as a thin-walled hollow tube. The tube is inserted in the slit in the eardrum so that there is communication between the outer ear and the middle ear to accommodate relative pressure changes between the atmosphere and the middle ear cavity. Flanges are formed on the medial and lateral ends of the tube for holding it in place in the eardrum.

The tube can be tapered, preferably with the portion having the smaller diameter on the side of the middle ear so that after the portion of the tube in contact with the eardrum dissolves, the larger portion of the tube drops easily out of the slit into the outer ear, while the smaller, inner portion drops into the middle ear cavity where it completely dissolves and is absorbed into the body.

While ventilation tubes are typically not maintained in the ear for longer than six months, the degradation rate of the biodegradable material from which the tube is formed can be adjusted to dissolve in a shorter or longer period of time to accommodate different desired time periods. This can be done by adjusting the molecular weight of the biodegradable material or making other adjustments in the chemical makeup or geometry of the material.

As discussed in greater detail below, the tube can be formed of a biodegradable material which is preferably selected from the following group: poly(DL-lactide); a copolymer of glycolide and DL-lactide or L-lactide; a copolymer of caprolactone and DL-lactide or L-lactide; and polycaprolactone. It is believed that other biodegradable materials such as poly(B-Benzyl-L-aspartate-co-L-leucine) could also be used. All or part of the ventilation tube can be formed of such biodegradable material depending on the use and function of the particular tube. If the tube is designed so that a portion will fall into the middle ear cavity after the portion of the tube which is in contact with the eardrum dissolves, that portion should also be formed of a biodegradable material so that it can dissolve into the human body without having to be surgically removed. The portion of the tube which falls outwardly into the outer ear does not have to be formed of a biodegradable material, but can be if manufacturing techniques make such a structure advantageous.

Such devices have the advantage of being removable without requiring additional surgery after removal, but still effectively perform the same function as existing ventilation tubes.

BRIEF DESCRIPTION OF THE DRAWINGS

For a better understanding of the present invention, reference may be made to the following description of an exemplary embodiment, taken in conjunction with the accompanying drawings, in which.

DETAILED DESCRIPTION OF AN EXEMPLARY EMBODIMENT

Figure 1:
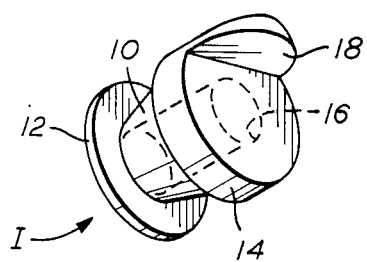
FIG. 1 is a perspective view of a ventilation tube formed according to the present invention.
Figure 2:
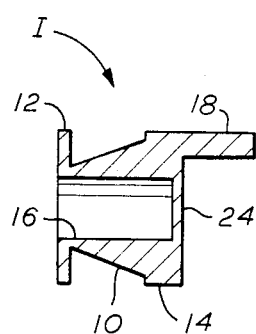
FIG. 2 is a side section view of the tube of FIG. 1 looking in the direction of arrows 2—2 as shown in FIG. 3.
Figure 3:
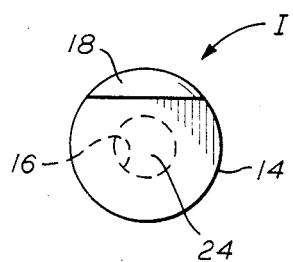
FIG. 3 is a plan view of the lateral end of the tube of FIG. 1.
Figure 4:
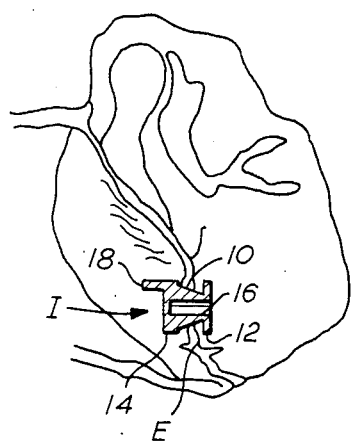
FIG. 4 is a sectional view of the middle ear showing, in particular, the ventilation tube of FIGS. 1–4 in situ.

An exemplary embodiment of the prosthetic device taught by the present invention is described in detail in conjunction with the drawings. Referring particularly to FIGS. 1 and 2, a prosthetic device in the form of a ventilation tube is designated generally by letter I. The tube I includes a shaft 10 with a flange 12 connected on its inner or medial end and a flange 14 connected at its outer or lateral end, the flanges 12 and 14 being formed perpendicular to the shaft 10. Together the flanges 12 and 14 resemble a "bobbin-type" configuration and, as shown in FIG. 4, hold the tube I in place after insertion and prevent it from slipping out of a slit formed in an eardrum E which separates an external ear canal from a middle ear cavity. The shaft 10 is formed as a tube with an axial passage 16. The outer surface of the shaft 10 between the flanges 12 and 14 is preferably tapered at an angle up to 70° from the horizontal, the reasons for which are described in greater detail below. The diameter of the outer surface of the tube I gradually increases from the medial end of shaft 10 toward the lateral end, providing a conical shape for the outer surface of the shaft 10.

A tab 18 is formed on the lateral side of the flange 14 so that the tube I can easily be gripped during insertion. A notch (not shown) can be formed in the lower quadrant of the medial flange 12 for easy insertion through the slit formed in the eardrum. For tubes of the type described above, the axial passage 16 has a minimum diameter of about 0.030" and an outside diameter of greater than 0.350".

The outer end of axial passage 16 can be covered by a porous membrane 24 which functions to prevent liquids such as water from entering the middle ear, but permits gas to flow from the middle ear and prevent a pressure buildup. The membrane 24 can be formed by a centrifugal casting technique from a silicone material or other polymers, including biodegradable ones. A silicone material available from Dow Chemical Company is connected to the tube I by a procedure using a solvent such as xylene to "weld" the membrane onto the lateral, outer flange 14 end of the tube I. The membrane 24 is preferably less than about 0.005" thick.

The ventilation tube I is installed using known techinques by inserting the medial flange 12 through an appropriately placed slit in the eardrum E, as shown in FIG. 4. The tube I is secured in the eardrum, the medial flange 12 and lateral flange 14 preventing the tube I from falling out.

The tube I is formed of a biodegradable material, e.g., a material that dissolves with time upon contact with moisture such as found in body fluids. Compounds which have been found to be suitable for this purpose are poly(DL-lactide), a copolymer of caprolactone and DL-lactide, a copolymer of glycolide and DL-lactide, and polycaprolactone. The tube I can be injection-molded into the desired configuration using standard injection-molding techniques or the tube I can be machined from rods of the biodegradable material.

Because the tube I is formed of a biodegradable material, when the portion of the tube I in contact with the ear dissolves in situ, the medial flange 12 falls into the middle ear where it will eventually dissolve. The lateral flange 14 falls outwardly into the external ear canal. The tapered shape of the outer surface of the tube I causes the smaller portion to fall in the middle ear and the larger portion to fall outwardly once the tube dissolves. If the tube I is formed with a membrane 24, such membrane being formed of a non-biodegradable material should be located in the lateral flange 14. Obviously, the portion of the tube I which falls outwardly could be formed of a non-biodegradable material since it does not remain in the body. Once tube I has dissolved and fallen out of its slit in the eardrum, the slit heals and the tube has been removed non-surgically.

The degradation time of the biodegradable material can selectively be altered through irradiation with gamma rays or other methods known to those skilled in the art such as adjusting chemical composition of the prosthesis or changing the size or shape, in order to adjust the functional life of the prosthesis. Preferably, such a tube I would not remain in place longer than 6 months, although longer periods of time are possible. For the gamma ray technique, the gamma rays should be above 2.5 Mrad to effect changes in the degradation rate, preferably in the range of about 2.5 Mrad to about 5.0 Mrad. This technique of setting degradation rate is preferable because the tube I can be simultaneously sterilized through the use of gamma rays; a lower level of between 1.5 Mrad to about 2.5 Mrad normally being used to sterilize such devices.

The following examples illustrate how ventilation tubes can be made in accordance with the present invention:

EXAMPLE I

Synthesizing of Poly(DL-lactide)

Poly(DL-lactide) was prepared from an 88% aqueous solution of lactic acid. Water was first removed from the lactic acid monomer to produce crude poly(DL-lactide). The DL-lactide was then formed by vacuum distillation with zinc oxide and the monomer was purified by recrystallization from ethyl acetate. The dehydrated, purified monomer was melted in a 140° C. oil bath with stirring. A stannous octoate catalyst (which could also be tetraphenyltin), was added to the monomer and the monomer allowed to react in the hot bath with stirring until it became too viscous to be stirred any further. The polymer was then cooled under a nitrogen atmosphere (since moisture and air would reverse the reaction), and dissolved in dichloromethane to remove any unreacted monomer and other impurities. The polymer was reprecipitated into methanol. After vacuum drying, the final viscosity range was 0.5 to 1.5 dL/g.

EXAMPLE II

Synthesizing the Lactide Glycolide Copolymers

The lactide/glycolide copolymer was prepared by first synthesizing the glycolide and DL-lactide monomers. The synthesis of DL-lactide is accomplished as in Example I, above.

Glycolide monomer was synthesized from a 67% aqueous solution of glycolic acid (also known as hydroxyacetic acid—$CH_2OHCOOH$). Water was removed from the glycolic acid by vacuum aspirated distillation at 120° C. The glycolic acid polymerized spontaneously upon removal of the water and the resulting low molecular weight polymer was then cracked to its dimer by adding antimony III oxide and distilling the dimer at 120° C. under vacuum. The resulting glycolide monomer was purified by recrystallization from ethyl acetate.

To prepare the 75/25 poly(DL-lactide-co-glycolide) the appropriate ratio of each monomer was mixed and melted in a 140° C. oil bath. Stannous octoate was added as a catalyst (although tetraphenyltin or antimony trifluoride could be used) and the reaction was carried out with stirring in the hot oil bath using lauryl alcohol as an initiator. The copolymer was then cooled under a nitrogen atmosphere and purified by dissolution in dichloromethane and then reprecipitated into methanol and dried under vacuum. The resulting viscosity range is 0.5 to 1.5 dL/g.

EXAMPLE III

Synthesizing the Lactide/Caprolactone Copolymer

The lactide/caprolactone copolymer used in an injection molding process was prepared from ε-caprolactone, which was obtained from Aldrich Chemical Company and purified by vacuum distillation, and DL-lactide which was synthesized as described above in Example I. The ε-caprolactone and DL-lactide monomers were then combined in appropriate ratios and melted in a 140° C. oil bath, polymerized with stannous octoate and then cooled under a nitrogen atmosphere. After purification in dichloromethane and methanol, and after vacuum drying, the viscosity range was 0.5 to 1.5 dL/g. The polycaprolactone used to prepare the tubes was PCL-700 commercially available from Union Carbide Corporation.

EXAMPLE IV

Extrusion of Machined Rods

Rods were extruded from the biodegradable polymers poly(DL-lactide) and a 75:25 mole ratio poly(DL-lactide-co-glycolide). The polymer was first pre-dried under vacuum for 24 hours to remove trapped moisture as before. The polymer was then placed in a Tinius Olsen Extrusion Plastometer Chamber with a 5/32 inch spinneret which was blocked to prevent loss of polymer during the equilibration period. The extrusion chamber was preheated to the desired temperature. For example, 95° C. is desired for the 75:25 poly(DL-lactide-co-glycolide) and 140° C. for the poly(DL-lactide). The polymer was then packed into the chamber and allowed to equilibrate 5 to 10 minutes. The Teflon block was removed and 5/32 inch rods were extruded, which were later machined into ear ventilation tubes. Ventilation tubes machined from poly(DL-lactide-co-glycolide) have a different degradation rate from those tubes machined from poly(DL-lactide).

EXAMPLE V

Injection Molding of the Polymer

First, moisture which might aggravate the degradation of polymer during the injection molding process was removed from the polymer. The mold was preheated in a Blue "M" forced air oven to a temperature approximately 10° cooler than the injection temperature. This allowed the polymer to remain molten as it flowed through the mold. The chamber of a Frohring Mini-Jector Injection Molder was heated to temperatures higher than the melting point of the polymer. [For example, 175° C. for the PCL-700 and 190° C. for the poly(DL-lactide).] The chamber of the Frohring Mini-Jector Injection Molder was packed with polymer and the polymer allowed to equilibrate for 5 to 10 minutes. The polymer was then injected into the preheated mold, annealed for 15 minutes, cooled in an ice bath for 15 minutes and the samples removed. The process was then repeated.

EXAMPLE VI

Effects of Copolymer Composition on Biodegradation Rates

Earlier work has been accomplished on testing the biodegradation rates for various copolymer compositions, which shows that such copolymers are useful in prosthetic devices of the type dealt with herein. This work was described in "Poly(Lactic acid) and Poly(-Lactide-co-glycolide) Contraceptive Delivery Systems," by Beck and Tice; *Long-Acting Steroid Contraception*, edited by Daniel R. Muskell, Jr., Raven Press (N.Y.) 1983, which is incorporated herein as though fully set forth.

EXAMPLE VII

Degradation of Polymers by Irradiation

A sample with a molecular weight of about 30,000 to about 120,000 was exposed to gamma radiation ranging from 2.5 Mrad to about 5.0 Mrad. The resulting molecular weight upon degradation may be calculated according to standard viscosity and gel permeation chromotography tests. As a general guide, 2.5 Mrads results in approximately a 25% reduction in molecular weight of the polymer, while radiation on the order of 4.5 to 5.0 Mrad results in approximately a 50% reduction of molecular weight of the polymer. Gamma radiation on the order of 1.5 to 2.5 Mrad results in a sterilization of the polymer.

This may be desired since a polymer of lower molecular weight results in faster degradation in the environment then does a polymer of higher molecular weight. A polymer of higher molecular weight, however, is easier to fabricate, and thus the irradiation process may be used to reduce the molecular weight of an already fabricated higher molecular weight polymer in order to effectuate faster degradation. By this means, the molecular weight and absorption time of the polymer may be adjusted by irradiation.

Polymers which have not undergone radiation such as polycaprolactone and poly L-lactide may take as many as two or three years to degrade in their environments, while others may degrade within a month for the same size samples.

The prosthesis in this invention can be made entirely of a material of a particular molecular weight and then irradiated in order to reduce that molecular weight and increase degradation. Also, it is conceivable that a portion of the prosthesis of this invention may be made of a polymer of a molecular weight lower than that of the remainder of the prosthesis. The lower molecular weight of material undergoes faster degradation and thus effectuates a break at the point of lowest molecular weight in the prosthesis and the remainder portion of the prosthesis with the higher molecular weight falls away.

In addition, the prosthesis may be made of a polymer of one molecular weight, but is made so that certain portions of the polymer prosthesis are thicker than others and thus would take longer to degrade.

Thus, there is provided a prosthetic device which is formed, at least in part, of a biodegradable material that is removable without additional surgery. While the invention may be modified or improved upon without departing from the spirit of the invention, it is contemplated that all such modifications and variations shall be within the scope of the appended claims.

What is claimed as the present invention is:

1. A prosthetic device formed of a biodegradable material and useful as a ventilation tube, comprising a shaft with an axial passage, an inner flange, an outer flange, at least a portion of the outer surface of the shaft being tapered, the diameter of the tapered portion of the outer surface increasing from the inner to the outer flange, so that the outer flange and any attached portion of the shaft are forced outwardly when said tapered portion of the shaft in contact with animal tissue biodegrades before other portions of the prosthesis.

2. The prosthesis of claim 1, and further including a membrane across the axial passage permeable to gas but impermeable to liquid.

3. The prosthesis of claim 1, wherein at least the portion of the shaft in contact with animal tissue is formed of a copolymer which is comprised of at least two biodegradable compounds having respective molecular weights of from about 30,000 to about 120,000.

4. The prosthesis of claim 1, wherein the material of said first section is selected from the group consisting of poly(DL-lactide); a copolymer of glycolide and DL-lactide or L-lactide; a copolymer of caprolactone and DL-lactide or L-lactide; and polycaprolactone.

5. A ventilation tube for insertion between the middle ear and outer ear, comprising:

a tube having an axial passage, the diameter of at least a portion of the outer surface of said tube increasing from the proximal end to the distal end of said tube;

an inner flange formed on the proximal end of said tube;

an outer flange formed on the distal end of said tube; and at least said tube and said inner flange being formed of material which biodegrades on contact with animal body fluids, so that when a portion of the tube in contact with animal fluids biodegrades, a break occurs in the tube and the inner flange will fall into the inner ear and biodegrade upon contact with animal fluids therein and the outer flange will fall outwardly into the outer ear.

6. The ventilation tube of claim 5, wherein said material which contacts said animal body fluids is selected from the group consisting of poly(DL-lactide); a copolymer of glycolide and DL-lactide or L-lactide; a copolymer of caprolactone and DL-lactide or L-lactide; and polycaprolactone.

7. The ventilation tube of claim 5, and further including a membrane across the axial passage of the tube permeable to gas but impermeable to liquid.

8. The ventilation tube of claim 5, wherein the biodegradable material is formed of a copolymer which is comprised of at least two biodegradable compounds having respective molecular weights of from about 30,000 to about 120,000.

* * * * *